(12) United States Patent
Liao et al.

(10) Patent No.: US 10,919,905 B2
(45) Date of Patent: Feb. 16, 2021

(54) POLYMORPHISM FOR IRINOTECAN FREE BASE

(71) Applicant: ScinoPharm Taiwan, Ltd., Tainan (TW)

(72) Inventors: Yuan-Xiu Liao, Tainan (TW); Yuan-Chang Huang, Tainan (TW)

(73) Assignee: ScinoPharm Taiwan, Ltd., Tainan (TW)

(*) Notice: Subject to any disclaimer, the term of this patent is extended or adjusted under 35 U.S.C. 154(b) by 0 days.

(21) Appl. No.: 16/830,561

(22) Filed: Mar. 26, 2020

(65) Prior Publication Data

US 2020/0361951 A1 Nov. 19, 2020

Related U.S. Application Data

(60) Provisional application No. 62/848,685, filed on May 16, 2019.

(51) Int. Cl.
*C07D 491/22* (2006.01)

(52) U.S. Cl.
CPC ........ *C07D 491/22* (2013.01); *C07B 2200/13* (2013.01)

(58) Field of Classification Search
None
See application file for complete search history.

(56) References Cited

U.S. PATENT DOCUMENTS

| 8,247,426 B2 | 8/2012 | Pozzi et al. |
| 2011/0087042 A1 | 4/2011 | Ray et al. |

FOREIGN PATENT DOCUMENTS

| CN | 108484624 A * | 9/2018 | ........... C07D 491/22 |
| WO | 03-074527 A1 | 9/2003 | |
| WO | 2015-107131 A1 | 7/2015 | |

OTHER PUBLICATIONS

Yangtze River Pharmaceutical Group, Translation of CN 108484624, pp. 1-9 (Year: 2018).*
Morissette et al, Advanced Drug Delivery Reviews, 56, pp. 275-300 (Year: 2003).*
International Search Report dated Jul. 17, 2020 for related PCT/SG2020/050214.
Written Opinion dated Jul. 17, 2020 for related PCT/SG2020/050214.
Kumler, I. et al., "Oral administration of irinotecan in patients with solid tumors: an open-label, phase I, dose escalating study evaluating safety, tolerability and pharmacokinetics", Cancer Chemotherapy and Pharmacology, 2019, [Published online] Nov. 8, 2018, vol. 83, No. 1, pp. 169-178.

* cited by examiner

*Primary Examiner* — Zinna Northington Davis

(74) *Attorney, Agent, or Firm* — Enshan Hong; VLP Law Group LLP

(57) ABSTRACT

Crystalline form S1 of irinotecan free base characterized by a powder X-ray diffraction pattern with peaks at about 8.7±0.2, 13.1±0.2, 14.5±0.2, 17.4±0.2, 18.4±0.2, 20.9±0.2, 24.0±0.2 and 27.5±0.2 degrees two-theta degrees two-theta, and crystalline form S2 of irinotecan free base characterized by a powder X-ray diffraction pattern with peaks at about 7.1±0.2, 10.6±0.2, 12.4±0.2, 20.6±0.2, 21.6±0.2 and 24.2±0.2 degrees two-theta.

13 Claims, 7 Drawing Sheets

POLYMORPHISM FOR IRINOTECAN FREE BASE

CROSS-REFERENCES TO RELATED APPLICATIONS

This application claims priority from U.S. Provisional Patent Application Ser. No. 62/848,685, which was filed on May 16, 2019. The entire content of this provisional application is incorporated herein by reference.

BACKGROUND OF THE INVENTION

The present application relates to crystalline forms of irinotecan free base and processes of making thereof.

Irinotecan is [1,4'-bipiperidine]-1'-carboxylic acid, (4S)-4,11-diethyl-3,4,12,14-tetrahydro-4-hydroxy-3,14-dioxo-1H-pyrano[3',4':6,7]indolizino[1,2-b]quinolin-9-yl ester, having the following formula:

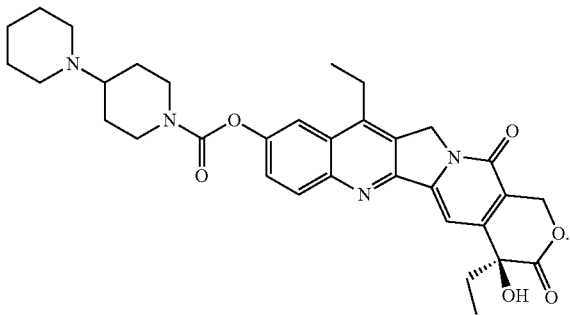 [SMILES: CCc1c2c(nc3ccc(OC(=O)N4CCC(N5CCCCC5)CC4)cc13)-c1cc3c(c(=O)n1C2)COC(=O)[C@]3(O)CC]

Unlike irinotecan hydrochloride, iriontecan in the form of free base has not been known to exist in different crystal forms. There is a need in the art for a stable, well-defined crystalline irinotecan free base, which may be conveniently used as an active pharmaceutical ingredient in the preparation of a pharmaceutical composition comprising irinotecan free base, and simple processes for preparing such a polymorph.

SUMMARY OF THE INVENTION

A first object of the present invention is to provide a crystalline form of iriontecan free base denominated as iriontecan base crystalline form S1 in the present application.

Irinotecan base crystalline form S1 is characterized by a powder x-ray diffraction pattern with peaks at about 8.7±0.2, 13.1±0.2, 14.5±0.2, 17.4±0.2, 18.4±0.2, 20.9±0.2, 24.0±0.2 and 27.5±0.2 degrees two-theta.

The crystalline form S1 may be prepared by a process comprising steps of: neutralizing an irinotecan acetic acid salt with sodium bicarbonate solution in dichloromethane to obtain a first mixture comprising an organic layer; filtering the first mixture; separating the organic layer from the first mixture; concentrating the separated organic layer; adding ethanol to the concentrated organic layer to precipitate the crystalline form S1 and obtain a second mixture; isolating the crystalline form S1 from the second mixture; washing the isolated the crystalline form S1 with ethanol; and then drying the crystalline form S1.

A second object of the present invention is to provide another crystalline form of iriontecan free base denominated as iriontecan base crystalline form S2 in the present application.

Irinotecan base crystalline form S2 of is characterized by a powder x-ray diffraction pattern with peaks at about 7.1±0.2, 10.6±0.2, 12.4±0.2, 20.6±0.2, 21.6±0.2 and 24.2±0.2 degrees two-theta.

The crystalline form S2 may be prepared by a process comprising steps of: dissolving irinotecan free base in dichloromethane at an elevated temperature to obtain an irinotecan free base solution; adding ethanol and then ethyl acetate to the irinotecan free base solution to precipitate the irinotecan free base and obtain a suspension. The precipitated crystalline form S2 is isolated from the suspension and washed with ethyl acetate and then dried.

DETAILED DESCRIPTION OF PREFERRED EMBODIMENTS OF THE INVENTION

The present application provides several crystalline forms of irinotecan free base, i.e., Forms S1-S3.

Figure 1:
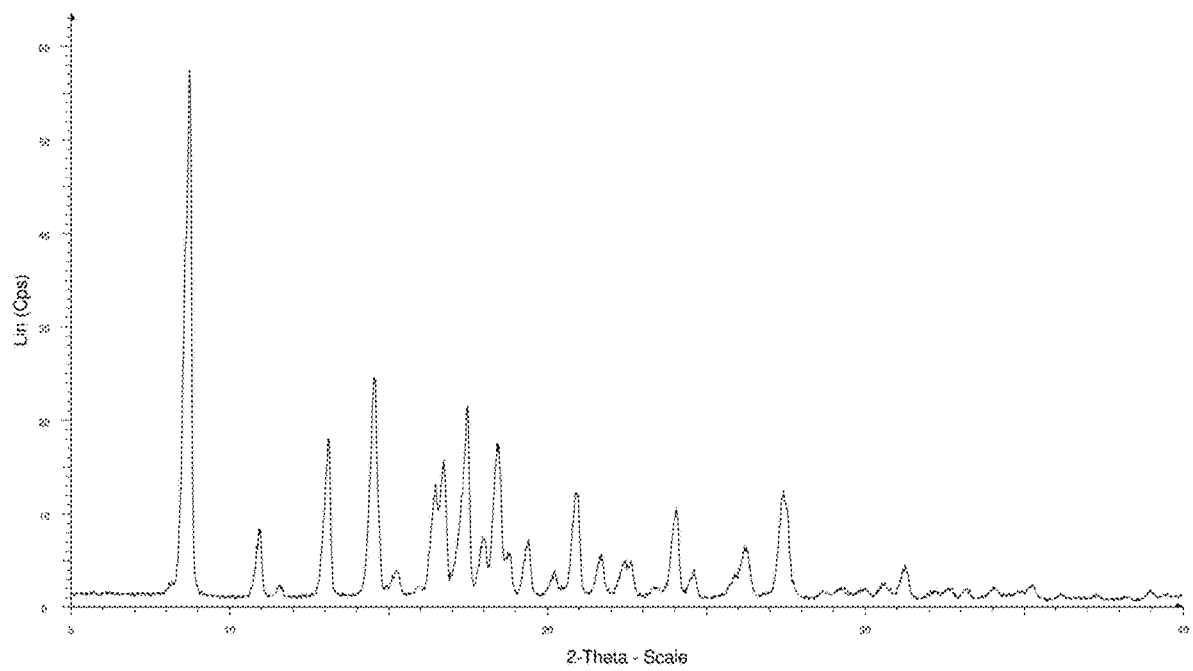
FIG. 1 illustrates a powder X-ray diffraction pattern of crystalline irinotecan free base form S1.

In accordance with one embodiment, crystalline form S1 of irinotecan free base is characterized by a powder x-ray diffraction pattern with peaks at about 8.7±0.2, 13.1±0.2, 14.5±0.2, 17.4±0.2, 18.4±0.2, 20.9±0.2, 24.0±0.2 and 27.5±0.2 degrees two-theta; preferably, form S1 is further characterized by a powder x-ray diffraction pattern with peaks at about 10.9±0.2, 11.6±0.2, 15.2±0.2, 16.4±0.2, 16.7±0.2, 18.0±0.2, 18.8±0.2, 19.4±0.2, 20.2±0.2, 21.7±0.2, 22.4±0.2, 22.5±0.2, 24.6±0.2, 26.2±0.2 and 31.3±0.2 degrees two-theta. As a preferred embodiment, the crystalline form S1 is preferably characterized by a powder X-ray diffraction pattern as substantially depicted in FIG. 1.

The crystalline form S1 may be characterized by a weight loss of about 3.1% at a temperature up to 150° C., as determined by thermal gravimetric analysis ("TGA"). The crystalline form S1 may be further characterized by data selected from a group consisting of: an endothermic peak at 50-150° C., an endothermic peak followed by an exothermic peak at 150-200° C., and two endothermic peaks with onset temperatures at 231.2° C. and 239.5° C., as determined by differential scanning calorimetry ("DSC"). Typically, the crystalline form S1 of irinotecan free base provided in the present application is a monohydrate form and preferably has a ~3.5% of water content, as analyzed by Karl Fischer titration ("KF").

Figure 4:
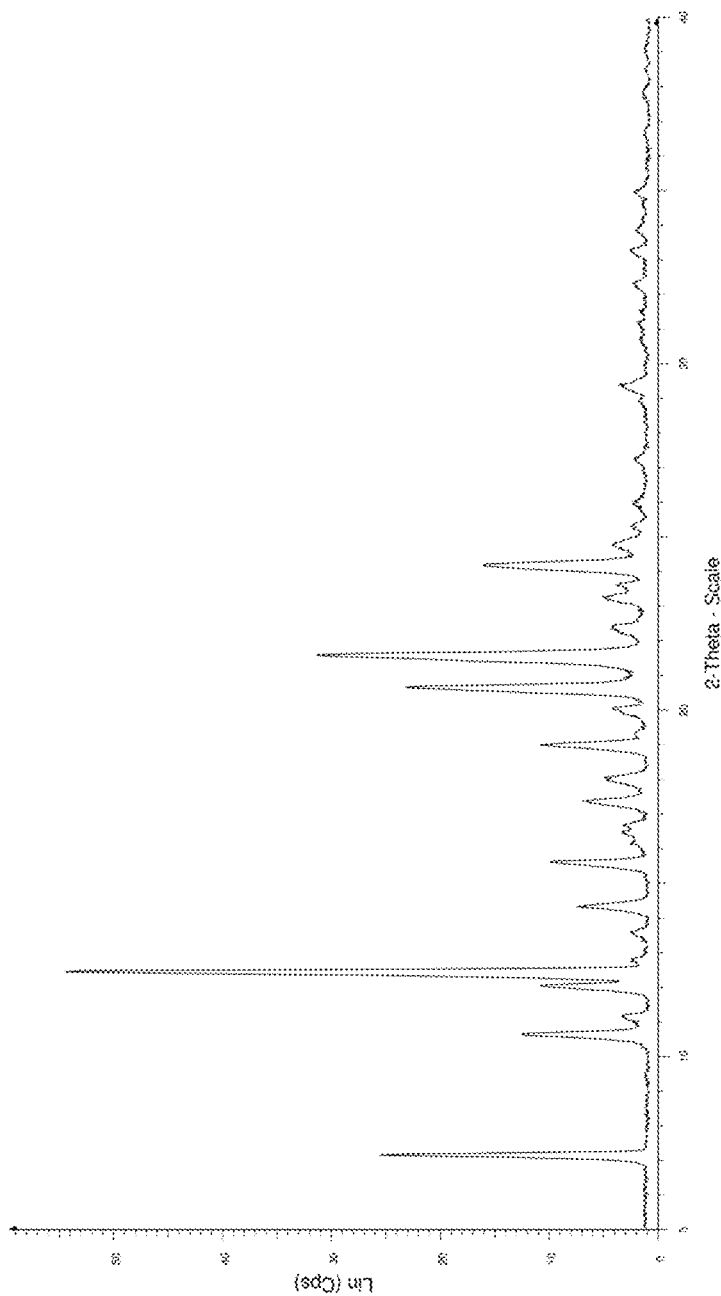
FIG. 4 illustrates a powder X-ray diffraction pattern of crystalline irinotecan free base form S2.

In accordance with a second embodiment, crystalline form S2 of irinotecan free base is characterized by a powder x-ray diffraction pattern with peaks at about 7.1±0.2, 10.6±0.2, 12.4±0.2, 20.6±0.2, 21.6±0.2 and 24.2±0.2 degrees two-theta; preferably, form S2 is further characterized by a powder x-ray diffraction pattern with peaks at about 12±0.2, 14.3±0.2, 15.6±0.2, 17.3±0.2, 19.0±0.2, 23.2±0.2 and 24.8±0.2 degrees two-theta. As a preferred embodiment, the crystalline form S2 is preferably characterized by a powder X-ray diffraction pattern as substantially depicted in FIG. 4.

The crystalline form S2 may be characterized by a weight loss of about 1.1% at a temperature up to 150° C., as determined by thermal gravimetric analysis ("TGA"). The crystalline form S2 may be further characterized by data selected from a group consisting of an endothermic peak with the onset temperature at 111° C. and an endothermic peak with maximum temperature at 235.7° C.

EXPERIMENTAL METHODOLOGY

X-Ray Powder Diffraction Analysis

X-ray Powder Diffraction patterns were collected on a Bruker AXS D8 diffractometer using Cu Kα1 radiation (40 kV, 40 mA), θ-2θ goniometer, and divergence of 10 mm slits, a Ge monochromator and LynxEye detector. The representative PXRD pattern was collected under ambient condition.

The details of the scanning parameters are:

Angular range: 5-40°

Step size: 0.02°

Scan speed: 0.6 sec/step.

Thermogravimetric Analysis (TGA)

TGA data was collected on a TA instrument Q500 TGA. Each sample (15-20 mg) was loaded onto a pre-tared platinum crucible and the balance and furnace were purged with nitrogen prior to the analysis with a flow rate set as 40±5 and 60±5 mL/min, respectively. The heating process was programmed to start at the ambient temperature and stop at 300° C. with a 10° C./min ramp.

Differential Scanning Calorimetry (DSC)

DSC data was collected on a TA Instrument MDSC Q200. Each sample (2-5 mg) was loaded onto a hermetic pan and the analysis was carried out under a constant flow of nitrogen (60 mL/min). The heating process was programmed to start from 30° C. with a 10° C./min ramp and stop at 270° C., respectively.

EXAMPLES

The following examples are provided to illustrate, but not to limit, the present invention.

Example 1

The preparation of the crystalline form S1 of irinotecan free base

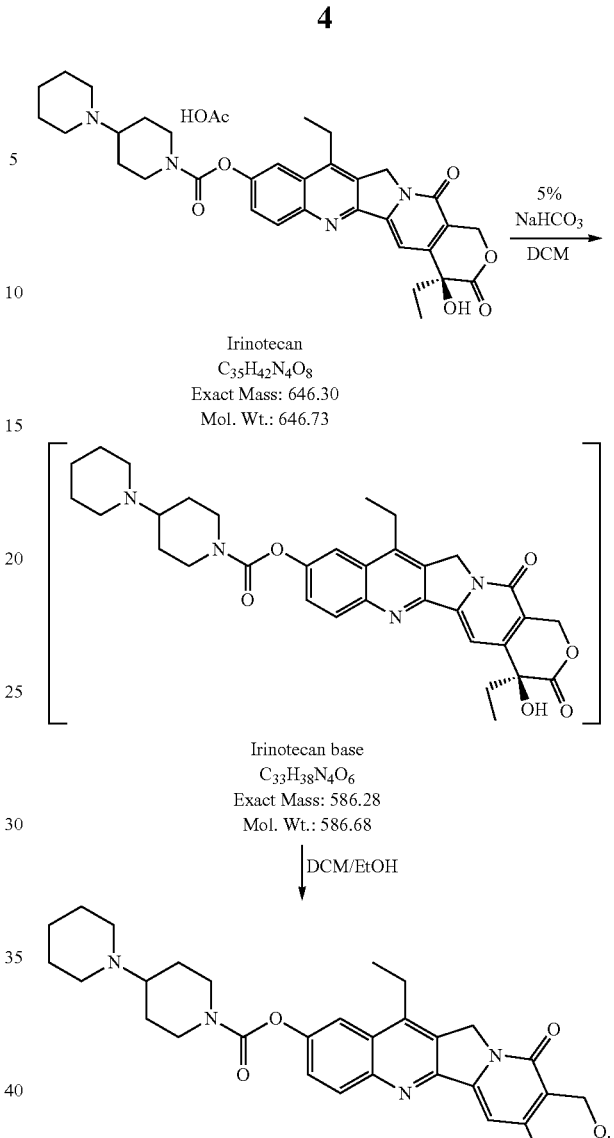

Irinotecan
$C_{35}H_{42}N_4O_8$
Exact Mass: 646.30
Mol. Wt.: 646.73

Irinotecan base
$C_{33}H_{38}N_4O_6$
Exact Mass: 586.28
Mol. Wt.: 586.68

Form S1
$C_{33}H_{38}N_4O_6$
Exact Mass: 586.28
Mol. Wt.: 586.68

Irinotecan. HOAc (150 g) and dichloromethane (1300 mL, 8.7 vol) were added to a 3 L flask at 20-30° C. Water (150 mL, 1 vol) and 5% sodium bicarbonate (600 mL, 4 vol) were added to neutralization to form an organic layer, which was then separated. The separated organic layer was washed with water (1500 mL, 10 vol) and then concentrated to about 600 mL. Ethanol (1650 mL, 11 vol) was added to the organic layer at 30-40° C. to obtain a mixture. The mixture was concentrated to about 1500 mL and then cooled to 20-30° C. and stirred at this temperature for 1 hr to obtain a suspension, which was then filtered to obtain a wet cake. The wet cake was dried to afford irinotecan free base form S1 (120.3 g).

The PXRD characteristics of the crystalline form S1 of irinotecan free base are reflected in the following table:

| Angle 2-Theta ° | Intensity Cps | Intensity % % |
| --- | --- | --- |
| 8.7 | 57.5 | 100 |
| 10.9 | 8.37 | 14.5 |
| 11.6 | 2.33 | 4.1 |
| 13.1 | 18.1 | 31.4 |
| 14.5 | 24.5 | 42.5 |
| 15.2 | 3.78 | 6.6 |
| 16.4 | 13.2 | 22.9 |
| 16.7 | 15.7 | 27.4 |
| 17.4 | 21.3 | 37 |
| 18 | 7.51 | 13 |
| 18.4 | 17.6 | 30.5 |
| 18.8 | 5.77 | 10 |
| 19.4 | 6.6 | 11.5 |
| 20.2 | 3.71 | 6.4 |
| 20.9 | 12.1 | 21.1 |
| 21.7 | 5.55 | 9.6 |
| 22.4 | 4.94 | 8.6 |
| 22.6 | 4.91 | 8.5 |
| 24 | 10.2 | 17.7 |
| 24.6 | 3.99 | 6.9 |
| 26.2 | 6.39 | 11.1 |
| 27.5 | 12.3 | 21.4 |
| 31.3 | 4.4 | 7.6 |

Example 2

The preparation of the crystalline form S2 of irinotecan free base

Irinotecan free base (10.5 g) and dichloromethane (104 mL, 10 vol) were added to a 500 mL flask at room temperature (20-30° C.) to obtain a first mixture. Ethanol (32 mL, 3 vol) was added to the mixture at 35-45° C. followed by ethyl acetate (52 mL, 5 vol) to obtain a second mixture. The second mixture was concentrated to about 140 mL (13 vol), and then ethyl acetate (63 mL, 6 vol) was added at 35-45° C. to obtain a third mixture. The third mixture was concentrated to cloud, held for 1 hr to obtain a slurry mixture. The slurry mixture was concentrated to about 140 mL (13 vol) to obtain a fourth mixture. After holding for 1 hr, the fourth mixture was cooled to 20-30° C. and filtered to obtain a wet cake. The wet cake was washed with ethyl acetate (52 mL, 5 vol) then dried to afford irinotecan free base form S2 (7.65 g).

The PXRD characteristics of the crystalline form S2 of irinotecan free base are reflected in the following table:

| Angle 2-Theta ° | Intensity Cps | Intensity % % |
| --- | --- | --- |
| 7.1 | 25.5 | 46.7 |
| 10.6 | 12.5 | 23 |
| 11.1 | 3.29 | 6 |
| 12 | 10.7 | 19.6 |
| 12.4 | 54.6 | 100 |
| 12.8 | 2.45 | 4.5 |
| 13.6 | 2.41 | 4.4 |
| 14.3 | 7.38 | 13.5 |
| 15.6 | 9.84 | 18 |
| 16.2 | 2.43 | 4.5 |
| 16.4 | 3.18 | 5.8 |
| 16.7 | 3.2 | 5.9 |
| 17.3 | 6.76 | 12.4 |
| 18 | 4.69 | 8.6 |
| 19 | 10.7 | 19.6 |
| 19.3 | 2.04 | 3.7 |
| 20 | 4.02 | 7.4 |
| 20.6 | 23.2 | 42.5 |
| 21.6 | 31.5 | 57.7 |
| 22.4 | 4.15 | 7.6 |
| 23.2 | 5 | 9.2 |
| 23.6 | 3.82 | 7 |
| 24.2 | 16.1 | 29.5 |
| 24.8 | 4.12 | 7.5 |
| 25.3 | 2.37 | 4.3 |
| 26 | 1.86 | 3.4 |
| 27.2 | 2.14 | 3.9 |
| 29.4 | 3.3 | 6 |
| 32.3 | 2.04 | 3.7 |
| 33.3 | 2.31 | 4.2 |

Example 3

The preparation of the crystalline form S3 of irinotecan free base

Figure 7:
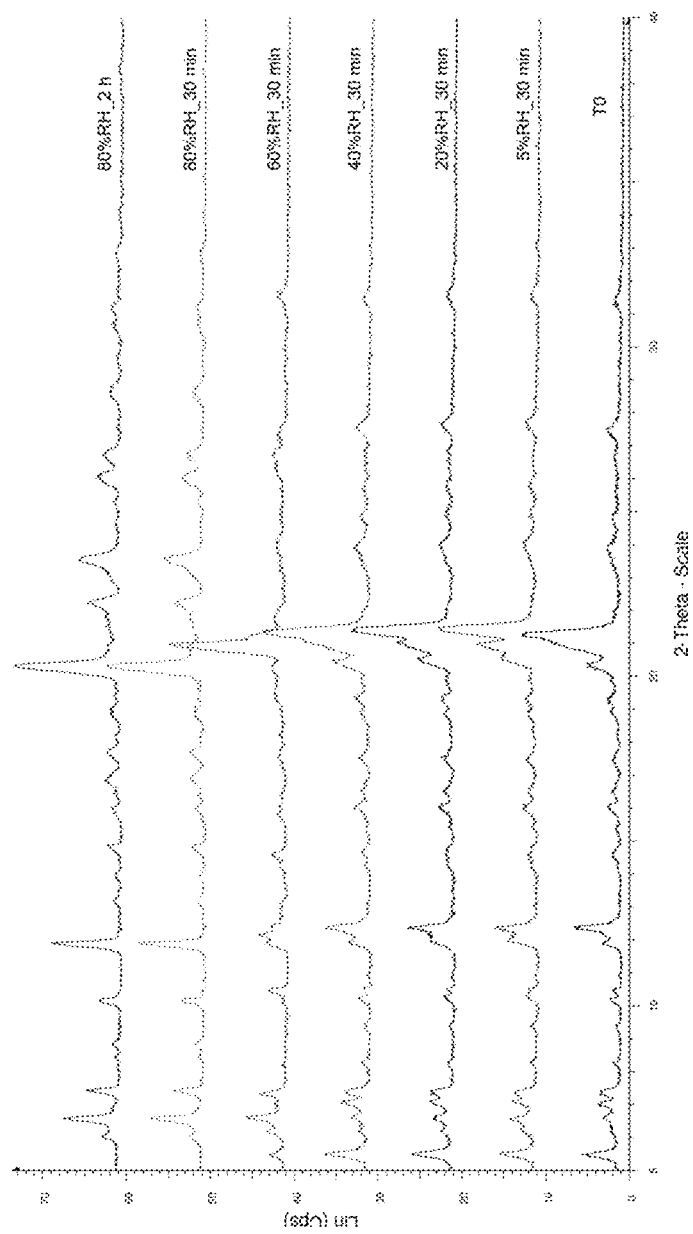
FIG. 7 illustrates the overlay powder X-ray diffraction patterns of crystalline form S3 irinotecan free base at different humidity conditions.

Irinotecan free base (119 g) and dichloromethane (1600 mL, 13.5 vol) were added to a 3 L flask at room temperature (20-30° C.) to obtain a first suspension mixture. Water (120 mL, 1 vol) and 5% sodium bicarbonate (480 mL, 4 vol) were added to the first mixture at room temperature. The suspension was filtered, and then the phases were allowed to separate, and an organic layer was saved. Water (600 mL, 5 vol) was added, and the phases were allowed to separate, and the organic layer was saved. The organic layer was concentrated to about 430 mL (3.6 vol). Ethyl acetate (1440 mL, 12 vol) was added to the concentrated organic layer at 25-35° C. to obtain a second mixture. The second mixture was concentrated to about 1665 mL (14 vol) then cooled to 15-25° C. to obtain a slurry mixture. The slurry mixture was filtered, and a wet cake was obtained and dried under the nitrogen to afford irinotecan free base form S3 (98.04 g). The Form S3 was studied by using variable humidity x-ray powder diffraction (VH-XRPD) to investigate the humidity effect on XRPD pattern (FIG. 7). When the sample was exposed at 5-40% RH, no significant change in diffraction peaks was observed. Once the sample was exposed at higher than 60% RH, the diffraction peaks changed, indicating that the humidity had impact on the diffraction peaks. The changes in diffraction peaks are reversible with the humidity being changed.

What is claimed is:

1. A crystalline form S1 of irinotecan free base characterized by a powder X-ray diffraction ("PXRD") pattern with peaks at about 8.7±0.2, 13.1±0.2, 14.5±0.2, 17.4±0.2, 18.4±0.2, 20.9±0.2, 24.0±0.2 and 27.5±0.2 degrees two-theta.

2. The crystalline form S1 of irinotecan free base of claim 1, further characterized by a powder X-ray diffraction pattern with further peaks at about 10.9±0.2, 11.6±0.2, 15.2±0.2, 16.4±0.2, 16.7±0.2, 18.0±0.2, 18.8±0.2, 19.4±0.2, 20.2±0.2, 21.7±0.2, 22.4±0.2, 22.5±0.2, 24.6±0.2, 26.2±0.2 and 31.3±0.2 degrees two-theta.

3. The crystalline form S1 of irinotecan free base of claim 1, characterized by a powder X-ray diffraction pattern as substantially depicted in FIG. 1.

Figure 2:
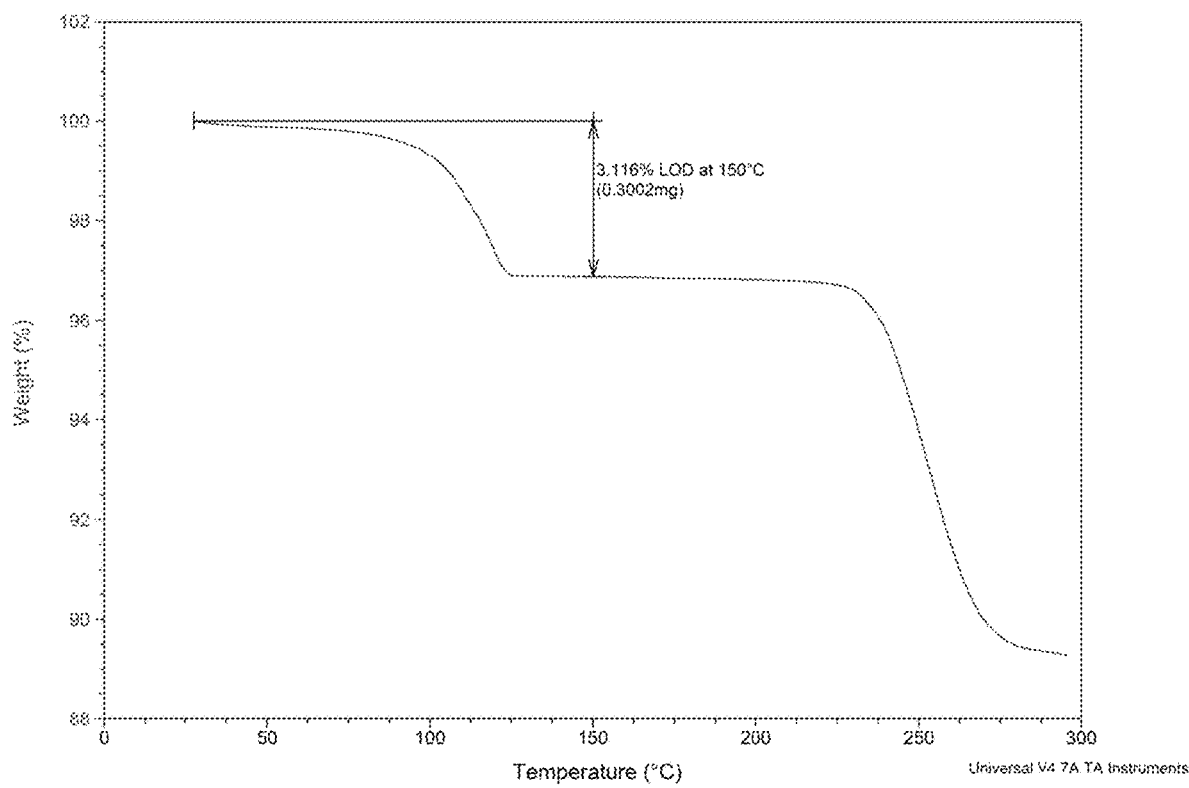
FIG. 2 illustrates a TGA thermogram for crystalline form S1 irinotecan free base.

4. The crystalline form S1 of irinotecan free base of claim 1, further characterized by thermal gravimetric analysis depicted in FIG. 2.

Figure 3:
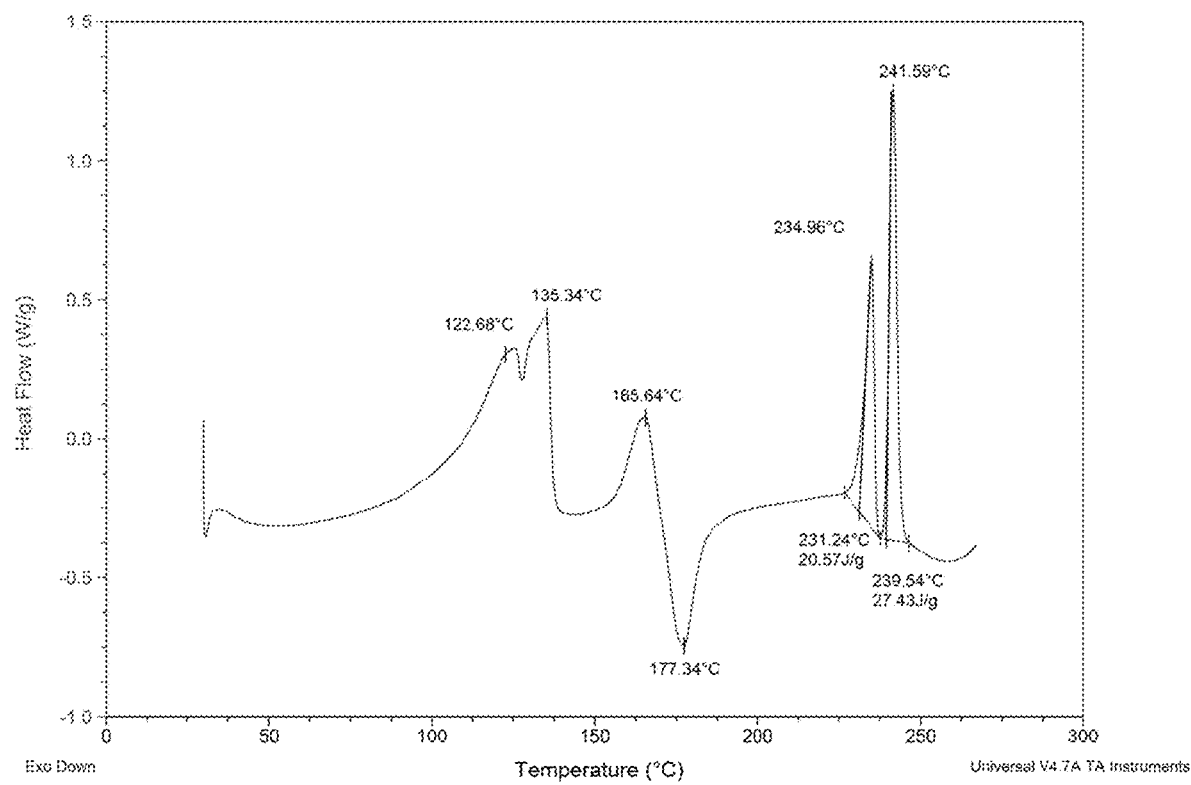
FIG. 3 illustrates a DSC thermogram for crystalline form S1 irinotecan free base.

5. The crystalline form S1 of irinotecan free base of claim 1, further by differential scanning calorimetry depicted in FIG. 3.

6. The crystalline form S1 of irinotecan free base of claim 1, wherein the crystalline form S1 is in a monohydrate form.

7. A process of making the crystalline form S1 of claim 1 comprising:
   a) neutralizing irinotecan acetic acid salt with sodium bicarbonate solution in dichloromethane to obtain a first mixture comprising an organic layer;
   b) separating the organic layer from the first mixture;
   c) washing the organic layer with water;
   c) filtering the washed organic layer of step c) and concentrating the organic layer;
   d) adding ethanol to the filtered and concentrated organic layer of step c) to precipitate the irinotecan free base form S1 and obtain a second mixture; and
   e) isolating the precipitated irinotecan free base S1 from the second mixture of step d).

8. A crystalline form S2 of irinotecan free base characterized by a powder X-ray diffraction ("PXRD") pattern with peaks at about 7.1±0.2, 10.6±0.2, 12.4±0.2, 20.6±0.2, 21.6±0.2 and 24.2±0.2 degrees two-theta.

9. The crystalline form S2 of irinotecan free base of claim 7, further characterized by a powder X-ray diffraction pattern with further peaks at about 12±0.2, 14.3±0.2, 15.6±0.2, 17.3±0.2, 19.0±0.2, 23.2±0.2 and 24.8±0.2 degrees two-theta.

10. The crystalline form S2 of irinotecan free base of claim 7, characterized by a powder X-ray diffraction pattern as substantially depicted in FIG. 4.

Figure 5:
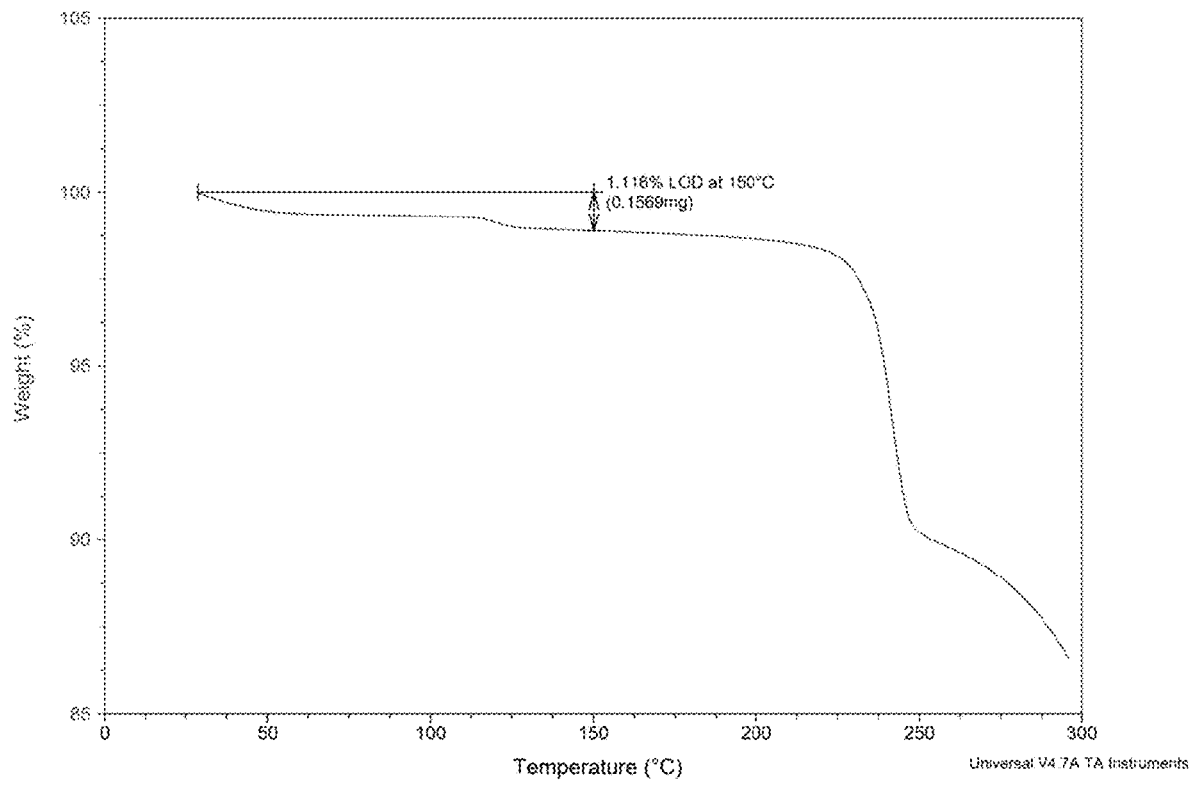
FIG. 5 illustrates a TGA thermogram for crystalline irinotecan free base form S2.

11. The crystalline form S2 of irinotecan free base of claim 7, further characterized by thermal gravimetric analysis depicted in FIG. 5.

Figure 6:
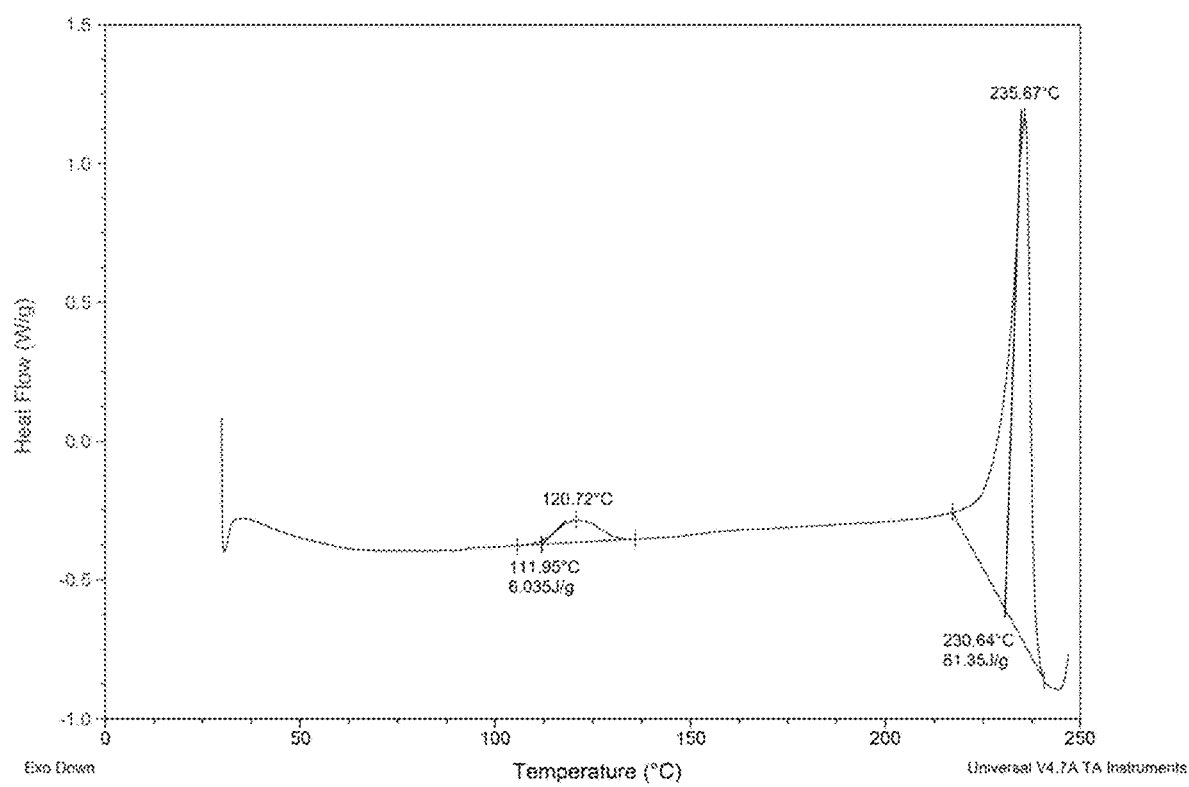
FIG. 6 illustrates a DSC thermogram for crystalline form S2 irinotecan free base.

12. The crystalline form S2 of irinotecan free base of claim 7, further characterized by differential scanning calorimetry depicted in FIG. 6.

13. A process of making the crystalline form S2 of claim 8 comprising:
   a) dissolving irinotecan free base in dichloromethane to produce a solution;
   b) adding ethanol and ethyl acetate to the solution of step a);
   c) concentrating the solution of step b) and adding ethyl acetate to form a suspension:
   d) filtering the suspension of step c) to form a wet cake; and
   e) drying the wet cake to produce the crystalline form S2 of irinotecan free base.

\* \* \* \* \*